United States Patent [19]

Kaluza et al.

[11] Patent Number: 5,153,122

[45] Date of Patent: Oct. 6, 1992

[54] TYPE II RESTRICTION ENDONUCLEASE MAMI

[75] Inventors: Klaus Kaluza, Habach; Gudrun Schmitz, Bernried; Michael Jarsch, Heilbrunn; Christoph Kessler, Munich, all of Fed. Rep. of Germany

[73] Assignee: Boehringer Mannheim GmbH, Mannheim, Fed. Rep. of Germany

[21] Appl. No.: 573,175

[22] PCT Filed: Nov. 25, 1989

[86] PCT No.: PCT/EP89/01460

§ 371 Date: Jul. 25, 1990

§ 102(e) Date: Jul. 25, 1990

[87] PCT Pub. No.: WO90/06361

PCT Pub. Date: Jun. 14, 1990

[30] Foreign Application Priority Data

Nov. 30, 1988 [DE] Fed. Rep. of Germany ....... 3840358

[51] Int. Cl.$^5$ .......................... C12P 19/34; C12N 9/22

[52] U.S. Cl. ...................... 435/91; 435/199; 435/822

[58] Field of Search ................ 435/196, 199, 91

Primary Examiner—Elizabeth C. Weimar
Assistant Examiner—Deborah Crouch
Attorney, Agent, or Firm—Felfe & Lynch

[57] ABSTRACT

New type II restriction endonuclease MamI has recognition sequence:

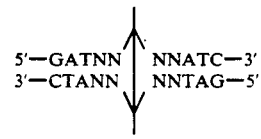

and a cleavage site indicated by the arrows. It is preferably obtained from microorganisms of the genus Microbacterium.

13 Claims, No Drawings

TYPE II RESTRICTION ENDONUCLEASE MAMI

FIELD OF THE INVENTION

The invention concerns the new type II restriction endonuclease MamI, a process for its isolation and its use.

BACKGROUND

Type II restriction endonucleases are endodeoxyribonucleases which are able to recognize and cleave particular DNA sequence. In this process, one phosphodiester bridge in each polynucleotide strand of the target sequence is hydrolyzed. Type II restriction endonucleases are thus of value for the analysis of DNA molecules. Although type II restriction endonucleases are known which are specific for numerous DNA sequences, there is still a need for further type II restriction endonucleases which are specific for DNA sequences which up to now have not been recognized by any of the known restriction endonucleases. The object of the invention is therefore to provide a new restriction endonuclease which is able to recognize and cleave a sequence which has not been recognized up to now by any such enzyme.

SUMMARY OF THE INVENTION

This object is achieved according to the present invention by a type II restriction endonuclease having the recognition sequence

and the cleavage site indicated by the arrows

DETAILED DESCRIPTION OF PREFERRED EMBODIMENTS

The new restriction endonuclease according to the present invention, which is denoted MamI hereafter, has a temperature optimum at ca. 37° C. The enzyme has good activity between pH 8.5 and pH 9.0 in 33 mmol/l Tris/HCl buffer with 0.5 mmol/l DTE (dithioerythritol), 10 mmol Mg acetate and 66 mmol K acetate. The pH optimum is at ca. pH 8.8. An isoschizomer for MamI is not known.

The recognition sequence can be confirmed by the complete digestion of the DNA's of the SV40 and adeno 2, viruses of the lambda phage, phix-174 viruses, of the phage derivatives M13mp8 and of the p-asmids pBR322 and pBR328. These DNA molecules are treated with MamI.

Table 1 shows a comparison of the cleavage site specificity observed experimentally with a cleavage site specificity determined by a computer for an enzyme which recognizes the sequence GATNNNNATC.

TABLE 1

| DNA | Number of cleavage sites determined experimentally | Number of cleavage sites determined by computer analysis | Fragment lengths (base pairs) determined experimentally | Fragment lengths (base pairs) determined by computer analysis | Cleavage positions determined by computer analysis |
|---|---|---|---|---|---|
| SV40 | 3* | 3 | 2400, 2400 | 1083, 1278, 2882 | at bp 1682, 2765, 4043 |
| phiX174 | 2 | 2 | 2400, 3000 | 2375, 3011 | at bp 341, 2716 |
| M13mp9 | 2 | 2 | 2900, 4800 | 2825, 4774 | at bp 1149, 3974 |
| pBR322 | 1* | 1 | undigested 4363 | at bp 1668 | |
| pBR328 | 0 | 0 | 0 | 0 | 0 |

*has a cleavage site which is not cleaved when the adenine is methylated.

The cleavage position within the recognition sequence of the enzyme can be determined on a M13 derivative having this recognition sequence at an interval of ca. 30–200 bases from the binding site of the universal sequencing primer (Messing, J. et al., (1981) Nucl. Acids Res. 9, 309–321). At first sequence reactions according to the dideoxy chain-termination method (Sanger, F. et al., (1977) Proc. Natl. Acad. Sci. USA 74, 560–564, Messing, J. et al., (1981) Nucl. Acids Res. 9, 309–321) are carried out on the single-stranded DNA of the M13 derivative with the universal sequencing primer.

Parallel to this, the sequencing primer is radioactively labelled at the 5' end with T4-polynucleotide kinase and $[\gamma$-$^{32}$P]ATP. After hybridization of this 5' end-labelled sequencing primer to the single-stranded M13 DNA, a partially double-stranded DNA is prepared in a "filling up" reaction with DNA-polymerase I, Klenow fragment and a deoxynucleotide triphosphate mixture of dATP, dCTP, dGTP and dTTP. This DNA, of which the newly synthesized strand is radioactively labelled at the 5' end, is now cleaved with the restriction endonuclease MamI. Half of the cleavage preparation is additionally treated with T4-DNA polymerase in the presence of a mixture of all four deoxynucleotide triphosphates in order to obtain flush DNA ends.

The analysis of the reaction products is carried out by electrophoresis on 8 mol/l urea, 5 % polyacrylamide sequencing gels and subsequent autoradiography. The results are interpreted according to Brown, N. L. and Smith, M. (Methods in Enzymology 65 (1980) 391–401). The position of the cleavage site is determined by a comparison of the distances of migration of the radioactively-labelled fragments with the sequencing ladder. The samples which were additionally treated with T4-DNA polymerase show identical distances of migration of the bands in comparison with the sample which was only cleaved with MamI. This therefore shows that MamI does not produce protruding but rather blunt DNA ends. The cleavage of MamI therefore has the following specificity within the recognition sequence:

The number of cleavage sites determined experimentally is identical to the number of cleavage sites for the sequence GATNNNNATC obtained by computer analysis with the different DNA's (Table I). In addition these data were also compared with the tables in Gene 10 (1980) 357-370.

MamI is preferably isolated by culturing microorganisms of the genus Microbacterium and isolating the enzyme from the cells. Microbacterium ammoniaphilum DSM 20156 is preferred. The usual biochemical methods of purification can be used for the isolation in which the presence of the enzyme in the respective fractions obtained can be easily tested on the basis of the cleavage of its recognition sequence. Lambda DNA e.g., is suitable as the substrate. The DNA fragments obtained are separated electrophoretically in agarose gels in buffer systems usually used for the fragment separation in the presence of ethidium bromide.

The microorganisms used for the isolation of the enzyme grow aerobically in Merck Standard I Medium.

The microorganism is deposited at the German Collection for Microorganisms, Gesellschaft für biotechnologische Forschung mbH, Mascheroder Weg 16, 3300 Braunschweig, BRD and has the deposit number DSM 20156. The optimal conditions for growth are pH 7.2-7.8 at 25° C. The doubling time is about 2 hours.

The enzyme is isolated and purified by the usual chemical and mechanical methods such as by high pressure dispersion, ultrasound or enzymatic lysis. In a preferred embodiment of the method according to the present invention the cells are subjected to an overpressure of 5 bar. The cell mass which forms in the process is resuspended in Tris HCl buffer, pH 8.0 which contains protease inhibitors. Subsequently the cells are lysed by means of a French press. The further purification of the supernatant is preferably carried out by means of affinity chromatography, molecular-sieve chromatography and ion-exchange chromatography. Heparin-Sepharose CL-6B which is carrier bound heparin for example (Pharmacia) is suitable as the material for the affinity chromatography. A suitable molecular sieve is, for example, Ultrogel ACA54 (LKB).

The product available under the name DEAE Sepharose Fast Flow ® (Pharmacia) is suitable as the anion-exchanger. Other chromatographic materials which are known to the expert are also suitable.

The following Examples elucidate the invention further.

EXAMPLE 1

*Microbacterium ammoniaphilum* DSM 20156 is cultured for 5 hours at 30° C. and harvested in the late logarithmic or stationary phase. Merck Standard Medium I is used as the culture medium.

The cell paste (30 g wet weight) is resuspended in 2.4 volumes buffer A (40 mmol/l Tris HCl, pH 8.0, 0.1 mmol/l EDTA, 7 mmol/l 2-mercaptoethanol), which contains protease inhibitors. Subsequently the cells are lysed by passing them three times through a French press at 23000 lb/inch² and the precipitate is separated off. The supernatant is subsequently fractionated on a heparin-Sepharose column which is pre-washed with NH₄Cl/buffer B. A gradient of 0-1 mol/l NH₄Cl is used for the elution. MamI is found in the fractions between 0.4 and 0.8 mol/l NH₄Cl. The active fractions are treated with 50 % ammonium sulphate and the precipitate is fractionated on an Ultrogel ® AcA54 column which has been previously equilibrated with buffer B to which 0.5 mmol/l NaCl is added. The active fractions are dialyzed against buffer B. Subsequently they are loaded on a Q-Sepharose ® Fast Flow column which has been equilibrated with buffer B. A gradient of 0-1.0 mol/l NaCl in buffer B is used for the elution. MamI is found in the fractions between 0.4 and 0.6 mol/l NaCl.

The active fractions are pooled and dialyzed against storage buffer (20 mmol/l Tris-HCl, pH 8.0, 10 mmol/l 2-mercaptoethanol and 100 mmol/l NaCl, 50 % (v/v) glycerol).

EXAMPLE 2

Determination of the activity

Definition of the enzyme units: 1 U MamI cleaves 1 μg lambda DNA within 1 hour at 37° C. in 25 μl final volume.

17.9 μl water and 3.6 μl lambda DNA (optical density: 5.6 OD/ml) as well as 1 μl MamI solution (1 U/μl) are added to a mixture of 2.5 μl incubation buffer (330 mmol/l Tris-HCl, pH 7.5/37° C., 100 mmol/l magnesium acetate, 660 mmol/l K-acetate, and 5 mmol/l DTE). The solution is incubated for 1 hour at 37° C., cooled on ice and 5 μl of a terminating reagent consisting of 7 mmol/l urea, 20 % (w/v) saccharose, 60 mmol/l EDTA and 0.01 % (w/v) bromophenol blue is added. Subsequently a separation is carried out by electrophoresis in 0.6 % agarose gels for 3-4 hours at 100 V. The bands obtained are identified by comparison with a DNA length standard.

We claim:

1. Type II restriction endonuclease having recognition sequence

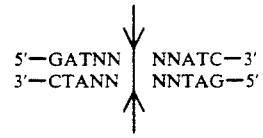

and a cleavage site indicated by the arrows.

2. Type II restriction endonuclease of claim 1, obtained from Microbacterium.

3. Type II restriction endonuclease of claim 1, obtained from *Microbacterium ammoniaphilium* DSM 20156.

4. Type II restriction endonuclease of claim 1, characterized by a temperature optimum of about 37° C. and a pH optimum from 8.5 to 9.0.

5. Process for isolation of a type II restriction endonuclease having recognition sequence

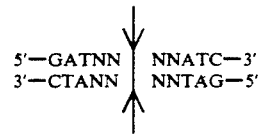

and a cleavage site indicated by the arrows, comprising culturing a Microbacterium microorganism which produces said type II restriction endonuclease and isolating said restriction endonuclease therefrom.

6. Process of claim 5, further comprising lysing said micro-organism to form a supernatant and isolating said restriction endonuclease from the supernatant.

7. Process of claim 6, further comprising subjecting said supernatant to affinity chromatography, molecular sieve chromatography, and anion-exchange chromatography.

8. Process of claim 7, comprising using carrier bound heparin for said affinity chromatography.

9. Method for obtaining a DNA sequence having terminal nucleotide sequence:

```
5'-GATNN-3'    5'-NNATG-3'
3'-CTANN-5' or 3'-NNTAG-5'
``` comprising contacting a sample of DNA with the restriction endonuclease of claim 12 and separating cleavage products produced thereby.

10. Process for the isolation of a type II restriction endonuclease having recognition sequence

and a cleavage site indicated by the arrows, comprising culturing a *Microbacterium ammoniaphilium DSM 20156* which produces said type II restriction endonuclease and isolating said restriction endonuclease therefrom.

11. Process of claim 10, further comprising lysing the microbacterium to form a supernatant and isolating said restriction endonuclease from the supernatant.

12. Process of claim 11, further comprising subjecting said supernatant to affinity chromatography, molecular sieve chromatography, and anion-exchange chromatography.

13. Process of claim 12, comprising using carrier bound heparin for said affinity chromatography.

* * * * *

UNITED STATES PATENT AND TRADEMARK OFFICE
CERTIFICATE OF CORRECTION

PATENT NO. : 5,153,122
DATED : October 6, 1992
INVENTOR(S) : Klaus Kaluza et al It is certified that error appears in the above-identified patent and that said Letters Patent is hereby corrected as shown below:

Col. 1, line 68, "p-asmids" should read --plasmids--.

Col. 2, line 17, Table 1, "4363" should be in column "Fragment lengths...computer analysis" and "at pb 1668" should be in the extreme right column.

Col. 5, line 16, new claim 9, "12" should read --1--.

Signed and Sealed this

First Day of March, 1994

*Attest:*

BRUCE LEHMAN

*Attesting Officer*     Commissioner of Patents and Trademarks